(12) United States Patent
Stratford et al.

(10) Patent No.: US 6,562,330 B1
(45) Date of Patent: May 13, 2003

(54) THERAPEUTIC USE OF POLYMERS

(75) Inventors: Peter William Stratford, Surrey (GB); Jane Louise Court, Surrey (GB); Andrew Lennard Lewis, Surrey (GB)

(73) Assignee: Biocompatibles Limited, Surrey (GB)

( * ) Notice: Subject to any disclaimer, the term of this patent is extended or adjusted under 35 U.S.C. 154(b) by 0 days.

(21) Appl. No.: 09/831,750

(22) PCT Filed: Nov. 12, 1999

(86) PCT No.: PCT/GB99/03796

§ 371 (c)(1),
(2), (4) Date: May 14, 2001

(87) PCT Pub. No.: WO00/28920

PCT Pub. Date: May 25, 2000

(30) Foreign Application Priority Data

Nov. 13, 1998 (EP) .............................................. 98309334

(51) Int. Cl.$^7$ ......................... A61K 31/74; A61K 9/00; A61K 47/30; A61K 47/34
(52) U.S. Cl. ................. 424/78.31; 424/78.08; 424/400; 514/772.2; 514/772.3
(58) Field of Search ................. 424/78.31, 78.08, 424/400; 514/772.2, 772.3

(56) References Cited

U.S. PATENT DOCUMENTS

| | | | |
|---|---|---|---|
| 3,467,604 A | 9/1969 | Michaels et al. | 260/2.5 |
| 4,994,069 A | 2/1991 | Ritchart et al. | 606/191 |
| 5,122,136 A | 6/1992 | Guglielmi et al. | 606/32 |
| 5,226,911 A | 7/1993 | Chee et al. | 606/191 |
| 5,667,767 A | 9/1997 | Greff et al. | 424/9.411 |
| 5,695,480 A | 12/1997 | Evans et al. | 604/264 |
| 5,702,361 A | 12/1997 | Evans et al. | 604/53 |
| 5,705,583 A * | 1/1998 | Bowers et al. | 526/277 |
| 5,749,894 A | 5/1998 | Engelson | 606/213 |

FOREIGN PATENT DOCUMENTS

| | | | |
|---|---|---|---|
| DE | 196 47 280 A1 | 10/1997 | A61F/2/01 |
| JP | 07-238124 | 9/1995 | C08F/230/02 |
| WO | 93/01221 | 1/1993 | C08F/246/00 |
| WO | 97/45131 | 12/1997 | A61K/33/04 |

OTHER PUBLICATIONS

Kataoka, K. et al., "Biomedical Behavior of Synthetic Polyion Complexes toward Blood Platelets", Makromol. Chem., 181, 1363–1373 (1980).

Kataoka, K. et al., "Effect of Charge and Molecular Structure of Polyion Complexes on the Morphology of Adherent Blood Platelets", Makromol. Chem., 179, 1121–1124 (1978).

XP–002102444, "Development of polyelectrolyte complexes as thromboresistant materials for use in components of artificial hearts", U.S. Clearinghouse Fed. Sci. Tech. Inform., PB Rep. (1969), PB–187793.

(List continued on next page.)

Primary Examiner—Thurman K. Page
Assistant Examiner—Blessing Fubara
(74) Attorney, Agent, or Firm—Sughrue Mion, PLLC

(57) ABSTRACT

An insoluble polymer is deposited in a body cavity for instance to embolize a vein or pack an aneurysm, the polymer having pendant zwitterionic groups to improve biocompatibility. The insoluble polymer is preferably formed by an in situ gelling step in which a charged, preferably soluble, polymer having pendant zwitterionic groups is introduced in the form of a composition in which it is soluble and is gelled by being mixed with a counterionically charged soluble polymer (polyelectrolyte), to form a polyion complex. Preferably the or each soluble polymer is formed by polymerizing ethylenically unsaturated monomers including a zwitterionic monomer, for instance 2-methacryloyloxyethyl-2'-trimethylammoniumethyl phosphate inner salt, an ionic monomer such as trimethylammonium alkyl(alk)acrylate or a sulphoalkyl(alk)acrylate and optionally a diluent monomer such as an alkyl(alk)acrylate.

28 Claims, 2 Drawing Sheets

OTHER PUBLICATIONS

XP–002102445, "Liquid blocking material for aneurysm–comprises solvent and polymer which hardens when solvent is dispersed in blood, useful for patients who cannot undergo general anaesthesia".

XP–002101612, "Complex polymer anion surfactant forming sheet contain amphoteric polymer metho acrylic acid di alkyl amino alkyl ester contain hydrophobic betaine hydrophobic unit".

* cited by examiner

THERAPEUTIC USE OF POLYMERS

The present invention relates to the use of a polymer in a method of treatment in which it is introduced into a body cavity under conditions whereby insoluble polymer is deposited in the body cavity. In the invention polymer having pendant zwitterionic groups is used, whereby biocompatibility is optimised.

The current chosen method for the treatment of aneurysms involves the packing of the aneurysm with platinum coils. Some work has been performed on the coating of these coils to provide a surface with increase thrombogenicity and render it biologically active by enabling the release of cellular growth factors and the like (German Patent DE-A-19647280). Others have concentrated on the use of polymer systems for embolising aneurysms, often simply by precipitating the polymer from a solution in a biocompatible solvent (WO-A-9745131). Specifically, a Japanese Group has had some success using a liquid composition containing a hardening polymer (cellulose acetate), with an X-ray contrast agent in a solvent such as DMSO. The polymer is caused to precipitate in-situ within the aneurysm when contacted with blood (JP-A-06-107549, *J. Neurosurg.*, 83(3), 531, 1995). Another approach has been to directly polymerise monomers in-situ, an example of which is a iron-acrylic compound which polymerises rapidly and is non-toxic (*J.Neurosurg.*, 47(2), 137, 1977). Yet another approach described in U.S. Pat. No. 5,749,894 is to introduce a coil and a polymeric composition which is melted by incident radiation and re-solidified in situ in the aneurysm. Examples of polymers are polyalkenes, poly(meth)acrylates, polyesters, polyamides and polysaccharides.

The use of polyion complexes in medical applications has been suggested for many years. Indeed, Michaels made reference to the use of such complex solutions for potting or encapsulating aneurysms, commenting that the materials were reasonably well tolerated by the tissue. Ioplex 101 (a complex poly(triethyl-(3 & 4)-vinylphenylammonium bromide) and poly(sodium vinyl benzenesulphonate)) has been examined intensively for biomedical usage (Vogel et al. *J.Macromol. Sci., Chem.*, 4, 675, 1970; Marshall et al., *J. Biomed Mater. Res.*, 4, 357, 1970; Bruck et al., *Ann. N.Y. Acad Sci.*, 283, 332, 1977). Analogues of this system have been studied to determine the effect of charge and structure on the complex and their behaviour towards blood platelets (Kataoka et al., *Makromol. Chem.*, 179, 1121, 1978 & 181, 1363, 1980) and have been used as encapsulating agents in the development of artificial liver support systems (Kataoka et a., *Jinko Zoki (Artificial Organs)*, 8 296, 1979).

Nakabayashi et al. have previously described the use of polyion complexes of polymers having zwitterionic pendant groups for the selective adhesion of platelets (*J. Biomed. Mater. Res.*, 28(11), 1347, 1994 by Ishihara, K. et al. Adv. Biomat. Biomed. Eng. Drug Delivery Syst. (1995) 227–228 by Ishihara, K. et al., and Japanese Patent JP-A-7-238124). Their invention claims specifically the use of a ternary polymer system consisting of 2-methacroyoyloxyethyl phosphorylcholine (MPC), butyl methacrylate (BMA) and sulfopropyl methacrylate (SPM) or trimethyl ammonium propyl methacrylate (TPM). Further to this, they define the compositions in which the MPC:BMA molar ratio is between 2:98–50:50, and the ratio of these two components to the ionic monomer (SPM or TPM) is between 98:2–80:20. These systems seem to have been designed to produce coatings with weak ionic interactions that have favourable properties in terms of platelet binding and activation. The polyion complexes described in these references are tested as coatings on glass beads and one of the products is said to be under test for use to encapsulate activated charcoal used for an artificial liver support system.

In the present invention there is provided a new use of a charged polymer in a method of manufacture of a composition for use in the method of treatment of a human or animal by therapy or diagnosis in which the charged polymer containing composition is introduced into a body cavity and is contacted with a separate composition comprising a polyvalently charged counterion whereby the polymer is rendered insoluble in the body cavity, and is characterised in that the charged polymer has zwitterionic pendant groups.

The present invention also includes the method of treatment itself.

In the present invention, the insoluble polymer is deposited as a gel in the body cavity. The polymer should be insoluble in situ, so that it remains in situ over a period of time, for instance at least several hours, days or weeks. A gel comprises a matrix of polymer and solvent distributed throughout the matrix. Preferably the solvent in the gel is aqueous and substantially free of organic solvent.

The gel depot may be used as a vehicle for delivery to the body cavity of therapeutically active agents, or diagnostic agents such as contrast agents. Contrast agents may, for instance, be introduced to allow medical practitioners to visualise the position of the insoluble polymer, which itself may be providing a therapeutic benefit, or diagnostic utility in a patient. According to a preferred aspect of the invention therefore the insoluble polymer is, in the body cavity, combined with a therapeutically active or imaging agent.

The gelled polymer may be a coating, or encapsulating agent, on particulate or non particulate solid material which is opaque to electromagnetic radiation (possibly radio frequency). The opaque material may, for instance, be an imaging agent such as described in U.S. Pat. No. 5,667,767 such as tantalum, tantalum oxide and barium sulphate, or as described in U.S. Pat. No. 5,695,480 including gold, tungsten and platinum. The opaque agent may be particulate or may be a solid material having a discrete physical shape, for instance being 1 mm or larger in size such as a metallic coil, filament, wire, mesh or tube. For instance coils as described in U.S. Pat. Nos. 4,994,069, 5,122,136, 5,226,911 or U.S. Pat. No. 5,702,361 may be included.

The present invention is particularly useful for embolising blood vessels, or for packing aneurysms. The polymer is thus used in methods analogous to those described in the prior art discussion above. The invention may also be used as a therapeutic or cosmetic filler, for instance for use following tumour excision, for enhancing lips or breasts, for improving muscle control, for instance sphincter muscles to control incontinence, for endoluminal gel paving, for the treatment of patent ductus arteriosus, or for replacement or supplement of synovial fluid.

The charged polymer is prior to insolubilisation, soluble, in the composition in which it is introduced into the body cavity. That composition is preferably aqueous. The polymer is thus preferably water-soluble. The counterion is also preferably soluble in the separate composition in which it is introduced into the body cavity. It is most convenient for the separate composition to be aqueous, so that it is preferred for the counterion to be introduced in a water-soluble form, in solution in an aqueous composition.

The two compositions may be mixed in the body cavity or immediately before being introduced into the body cavity. Preferably they are introduced using a catheter designed for the purpose, which has separate lumens for each composition and means for allowing contact and mixing of the compositions immediately before delivery of the insoluble, usually gel form, polymer from the catheter into the desired location in a body cavity.

The counterion may be inorganic or organic. It may be a di- or tri-valently charged soluble ion, for instance a metal cation, or a multivalent oxyanion. Calcium ions are suitable multivalent cations.

Preferably in the invention, the counterion is a polyelectrolyte. The counterionic charges of the two polymers attract one another when the polymers are intimately mixed, thereby insolubilising (gelling) the blend. This blend is consequently a polyion (or polyelectrolyte) complex. At least one of the polymers forming the polyion complex should have zwitterionic pendant groups. Preferably both polymers have zwitterionic pendant groups. The charged polymer which has an essential feature pendant zwitterionic groups, may be anionic or cationic but is preferably anionic. The counterion is thus preferably cationic.

In some embodiments of the present invention, a polycationic polymer will have permanently cationic pendant groups. These may be quaternary ammonium or phosphonium or tertiary sulphonium groups. In other embodiments, the cationic group may not be a permanent cation. It may be a weak or a strong base. For instance it may be selected so as to provide pH sensitivity whereby the degree of attraction between the two first polymers may be controlled by the pH.

Likewise, the anion may be the anion of a weak or strong acid, selected so as to be pH sensitive or insensitive within a predetermined pH range, as desired.

A suitable cationic group is a group $N^+R^1_3$, $P^+R^1_3$ or $S^+R^1_2$ in which the groups $R^1$ are the same or different and are each hydrogen, $C_{1-4}$-alkyl or aryl (preferably phenyl) or two of the groups $R^1$ together with the heteroatom to which they are attached from a saturated or unsaturated heterocyclic ring containing from 5 to 7 atoms. Preferably the cationic group is permanently cationic, that is each $R^1$ is other than hydrogen. Preferably the cationic group is $N^+R^1_3$ in which each $R^1$ is $C_{1-4}$-alkyl, preferably methyl.

Suitable anionic groups are carboxylate, carbonate, sulphonate, sulphate, phosphonate or phosphate. Preferably the anionic group is monovalent. A sulphonate group is particularly convenient.

In a polyion complex used in the invention, the polycationic polymer and polyanionic polymer are preferably used in ratios so as to provide a ratio of equivalents of cationic groups and anionic groups in the range 2:1 to 1:2. Preferably the anions are present in approximately equivalent amount to the cation so that the ratio is preferably in the range 1.5:1 to 1:1.5, or preferably 1.2:1 to 1:1.2, for instance about 1:1.

In the gelled condition the level of zwitterionic groups is preferably in the range 1 to 75 mole %, preferably 20 to 50%, based on the total moles of monomer from which the polymer(s) forming the insoluble polymer are formed (in the preferred embodiment where the charged polymer(s) is formed from ethylenically unsaturated monomers including zwitterionic monomer).

The amount of ionic monomer in an ionic polymer comprised in the charged polymer is preferably at least 1 mole %, more preferably at least 5 mole %, for instance at least 10 mole %. Where the amount is higher than about 30 or 40 mole % (and the counterionic charges in a PIC are approximately balanced) the or each polymer should preferably also include at least 20%, preferably at least 30% zwitterionic monomer.

For the preferred embodiment in which the charged polymer comprises at least one ionically charged polymer including zwitterionic pendant groups, the ratio of zwitterionic ionic groups is preferably in the range 5:1 to 1:5, preferably 2:1 to 1:3.

The total content of ionic and zwitterionic monomer in the charged polymer and in preferred counterion is preferably at least 25 mole %, more preferably at least 30%, more preferably at least 40%, up to 100%, more preferably up to 80%, most preferably in the range 50 to 70%. The remaining components of the polymer(s) are non-ionic monomer, which may act primarily as diluent or may confer desirable physical properties on the polymer(s). A non-ionic, monomer may comprise a hydrophobic pendant group.

The ratio of anionic to cationic polymer and the relative amounts of zwitterionic and hydrophobic diluent groups in a polyion complex may be judged by determining the gel properties of a gel, usually an aqueous gel formed by mixing the counterionic polymers from solutions each containing one of the polymers. A suitable technique for investigating the gel properties is described in Example 3 below.

The zwitterionic pendant group of the polymer used in the invention may have an overall charge, for instance by having a divalent centre of anionic charge and monovalent centre of cationic charge or vice versa or by having two centres of cationic charge and one centre of anionic charge or vice versa. Preferably, however, the zwitterion has no overall charge and most preferably has a centre of monovalent cationic charge and a centre of monovalent anionic charge.

Preferably the centre of cationic charge in the zwitterionic group is permanent, that is it is preferably a quaternary ammonium or phosphonium or a tertiary sulphonium group. Preferably the anion is permanent, that is it is substantially completely ionised at in vivo pH's, for instance at pH's in the range 5 to 8. It is preferably a phosphate, phosphonate, sulphate or sulphonate anion.

The zwitterionic group may be a betaine group (ie in which the cation is closer to the backbone than the anion), for instance a sulpho-, carboxy- or phospho-betaine. A betaine group should have no overall charge and is preferably a carboxy- or sulpho-betaine. If it is a phosphobetaine the phosphate terminal group must be a diester, i.e., be esterified with an alcohol. Such groups may be represented by the general formula I

   I in which $X^2$ is a valence bond, —O—, —S— or —NH—, preferably —O—;

V is a carboxylate, sulphonate or phosphate diester (monovalently charged) anion;

$R^2$ is a valence bond (together with $X^2$) or alkanediyl, —C(O)alkanediyl- or —C(O)NHalkanediyl preferably alkanediyl and preferably containing from 1 to 6 carbon atoms in the alkanediyl chain;

the groups $R^3$ are the same or different and each is hydrogen or alkyl of 1 to 4 carbon atoms or the groups $R^3$ together with the nitrogen to which they are attached form a heterocyclic ring of 5 to 7 atoms; and $R^4$ is alkanediyl of 1 to 20, preferably 1 to 10, more preferably 1 to 6 carbon atoms.

One preferred sulphobetaine monomer has the formula II

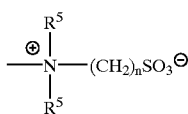

where the groups $R^5$ are the same or different and each is hydrogen or $C_{1-4}$ alkyl and n is from 2 to 4.

Preferably the groups $R^5$ are the same. It is also preferable that at least one of the groups $R^5$ is methyl, and more preferable that the groups $R^5$ are both methyl.

Preferably n is 2 or 3, more preferably 3.

Alternatively the zwitterionic group may be an amino acid moiety in which the alpha carbon atom (to which an amine group and the carboxylic acid group are attached) is joined through a linker group to the backbone of polymer A. Such groups may be represented by the general formula III

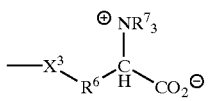

in which $X^3$ is a valence bond, —O—, —S— or —NH—, preferably —O—, $R^6$ is a valence bond (optionally together with $X^3$) or alkanediyl, —C(O)alkanediyl- or —C(O)NHalkanediyl, preferably alkanediyl and preferably containing from 1 to 6 carbon atoms; and the groups $R^7$ are the same or different and each is hydrogen or alkyl of 1 to 4 carbon atoms, preferably methyl, or two of the groups $R^7$, together with the nitrogen to which they are attached, form a heterocyclic ring of from 5 to 7 atoms, or the three group $R^7$ together with the nitrogen atom to which they are attached form a fused ring structure containing from 5 to 7 atoms in each ring.

Preferably the zwitterion has the formula IV

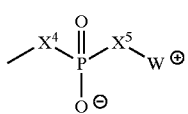

in which the moieties $X^4$ and $X^5$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group.

Preferably W contains as cationic group an ammonium group, more preferably a quaternary ammonium group.

The group $W^+$ may for example be a group of formula —$W^1$—$N^+R^8_3$, —$W^1$—$P^+R^9_3$, —$W^1$—$S^+R^9_2$ or —$W^1$-$Het^+$ in which:

$W^1$ is alkanediyl of 1 or more, preferably 2–6 carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups; and either the groups $R^8$ are the same or different and each is hydrogen or alkyl of 1 to 4 carbon atoms, preferably methyl, or aryl, such as phenyl or two of the groups $R^8$ together with the nitrogen atom to which they are attached form a heterocyclic ring containing from 5 to 7 atoms or the three groups $R^8$ together with the nitrogen atom to which they are attached form a fused ring structure containing from 5 to 7 atoms in each ring, and optionally one or more of the groups $R^8$ is substituted by a hydrophilic functional group, and the groups $R^9$ are the same or different and each is $R^8$ or a group $OR^8$, where $R^8$ is as defined above; and Het is an aromatic nitrogen-, phosphorus- or sulphur-, preferably nitrogen-, containing ring, for example pyridine.

Preferably $W^1$ is a straight-chain alkanediyl group, most preferably 1,2-ethanediyl.

Preferred groups of the formula IV are groups of formula V:

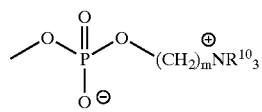

where the groups $R^{10}$ are the same or different and each is hydrogen or $C_{1-4}$ alkyl, and m is from 1 to 4.

Preferably the groups $R^{10}$ are the same. It is also preferable that at least one of the groups $R^{10}$ is methyl, and more preferable that the groups $R^{10}$ are all methyl.

Preferably m is 2 or 3, more preferably 2.

Alternatively the ammonium phosphate ester group V may be replaced by a glycerol derivative of the formula VB, VC or VD defined in our earlier publication no WO-A-93/01221.

Preferably the polymer or polymers having a pendant zwitterionic group are wholly synthetic, although under some circumstances it may be desirable to use derivatives of natural polymers. Preferably the polymer(s) is formed from radical polymerisable ethylenically unsaturated monomers including a monomer of the formula VI

YBX     VI wherein

B is a straight or branched alkanediyl, alkanediyloxaalkanediyl or alkanediyloligo(oxaalkanediyl) chain optionally containing one or more fluorine atoms up to and including perfluorinated chains or, if X or Y contains a terminal carbon atom bonded to B, a valence bond;

X is the zwitterionic group; and

Y is an ethylenically unsaturated polymerisable group selected from

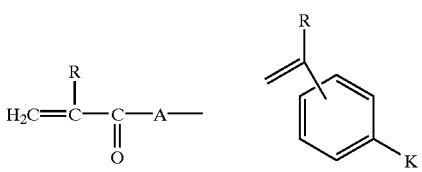

CH₂=C(R)—CH₂—O—, CH₂=C(R)—CH₂OC(O)—, CH₂=C(R)OC(O)—, CH₂=C(R)—O—, CH₂=C(R)CH₂OC(O)N(R¹¹)—, R¹²OOCCR=CRC(O)—O—, RCH=CHC(O)O—, RCH=C(COOR¹²)CH₂—C(O)—O—,

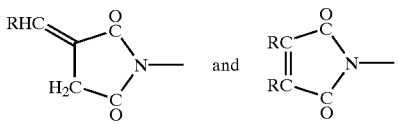

wherein:

R is hydrogen or a $C_1$–$C_4$ alkyl group;

$R^{11}$ is hydrogen or a $C_1$–$C_4$ alkyl group or $R^{11}$ is —B—X where B and X are as defined above; and $R^{12}$ is hydrogen or a $C_{1-4}$ allyl group or BX where B and X are as defined above;

A is —O— or —NR¹¹—;

K is a group —(CH₂)$_p$OC(O)—, —(CH₂)$_p$C(O)O—, —(CH₂)$_p$OC(O)O—, —(CH₂)$_p$NR¹³—, —(CH₂)$_p$NR¹³C(O)—, —(CH₂)$_p$C(O)NR¹³—, —(CH₂)$_p$NR¹³C(O)O—, —(CH₂)$_p$OC(O)NR¹³—, —(CH₂)$_p$NR¹³C(O)NR¹³— (in which the groups $R^{13}$ are the same or different), —(CH₂)$_p$O—, —(CH₂)$_p$SO₃—, or, optionally in combination with B, a valence bond and p is from 1 to 12 and $R^{13}$ is hydrogen or a $C_1$–$C_4$ alkyl group;

Preferably Y is a group CH₂=C(R)COA—, in which R is H or methyl, preferably methyl, and in which A is preferably O.

B is preferably an alkanediyl group of 1 to 12, preferably 2 to 6 carbon atoms, most preferably group (CH₂)$_q$ in which q is 2 to 6.

Where the polymer having a zwitterionic group is part of a polyion complex, the polymer is formed by including in the ethylenically unsaturated monomers an ionic monomer of the formula VII $$Y^1B^1Q \qquad \text{VII}$$

in which $Y^1$ is selected from the same groups as Y;

$B^1$ is selected from the same groups as B; and

Q is an ionic group or ionisable.

Q may be a cationic group $Q^1$ or an anionic group $Q^2$. A cationic group $Q^1$ is preferably as described above. An anionic group $Q^2$ is preferably selected from the groups listed above.

Another suitable type of cationic monomer copolymerisable with ethylenically unsaturated monomers is diallyl dialkyl ammonium halide, for instance diallyl dimethyl ammonium chloride.

The ethylenically unsaturated monomers preferably further comprise nonionic monomer. The nonionic monomer may be selected so as to confer desired solubility, hydrophilicity or hydrophobicity properties upon the polymer bearing zwitterionic pendant groups. The nonionic monomer may also confer on the polymer physical characteristics which affect the mechanical characteristics of the insoluble polymer in situ. For instance hydrophobic groups may provide inter or intramolecular interactions with other hydrophobic groups, or with substrates or biological compounds in situ which render the insoluble polymer particularly suitable for the desired application.

Preferably a nonionic monomer has the general formula VIII $$Y^2R^{14} \qquad \text{VIII}$$

in which $Y^2$ is selected from the same groups as Y; and $R^{14}$ is a nonionic organic group which is an optionally substituted $C_{1-24}$-alkyl or -alkenyl group. Optional substituents in the alkyl or alkenyl group are hydroxyl groups; halogen atoms, alkoxy and oligo-alkoxy groups, in which the alkoxy groups have 1–6, preferably 2 or 3 carbon atoms; aryl groups, preferably optionally substituted phenyl groups; optional substituents in a phenyl group being hydroxyl, halogen atoms or alkyl groups; acyl groups, especially $C_{1-6}$-alkanoyl groups; acyloxy groups, especially $C_{1-6}$-alkanoyloxy groups; acylamino groups, especially $C_{1-6}$-alkanoyl amino, in any of which alkanoyl groups there may be substituents selected from halogen atoms and hydroxyl groups, and alkoxy groups. Preferred groups $R^{14}$ are $C_{1-24}$-unsubstituted alkyl, more preferably $C_{4-18}$-alkyl.

A nonionic monomer is preferably present in the ethylenically unsaturated monomers from which the charged polymer and/or the counterionic polyelectrolyte are formed in a molar amount in the range 1–75%, preferably 20 to 70%, more preferably 30–50%.

A particularly preferred use of the invention is in the treatment of aneurysms. The charged polymer and counterion could be mixed via a catheter, in the form of aqueous solutions or dispersions, to form a gel in situ within the aneurysm void. Once filled the aneurysm would have no void space for the blood to occupy and the danger of rupture of the blood vessel would be removed.

The zwitterionic groups of the gelled (insoluble) polymer are believed to confer biocompatibility, minimising response from the inner lining of the aneurysm or other tissue or biological fluids in contact with the second polymer in the body cavity.

Figure 1:
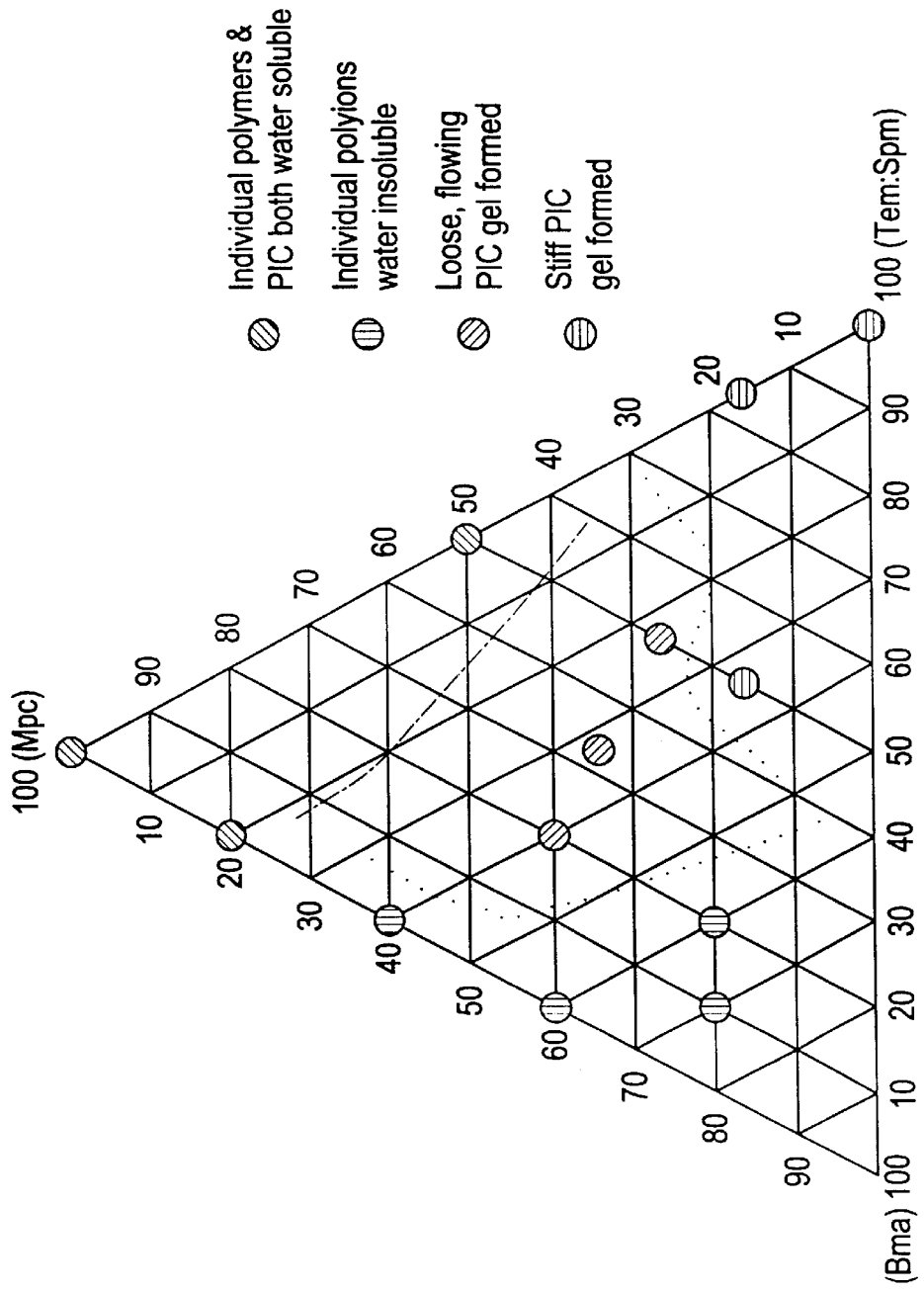
FIG. 1 is a phase diagram for the formation of polyion complexes from systems based on Mpc$_x$Bma$_y$Tem$_z$ and Mpc$_x$Bma$_y$Spm$_z$ (for abbreviations, see below)

The invention is illustrated further in the accompanying examples. In these examples, the following standard methods are used:

Inherent Viscosity

20% w/v solutions were made of each polymer using deionised water. The solution was subjected to a flow test (shear rate 1–1999 s⁻¹) using a TA Instruments CSL²-100 Rheometer fitted with a 6 cm 2° cone at a temperature of 37° C. From the resulting viscosity vs. shear rate trace, the viscosity (Pa.s) of the solution was determined by taking the value at 200 s⁻¹.

Fibrinogen Adsorption

This test is carried out substantially as described in WO-A-93/01221.

Bicinchoninic Acid Protein Assay

Assessment of protein adsorption was carried out using the Micro-Bicinchoninic Acid (m-BCA) Protein Assay (Pierce & Warriner kit), which relies on the colourimetric detection of a Cu(I) complex with BCA produced upon protein reduction of Cu(II) to Cu(I). Coated and uncoated PET strips were prepared as described for the immunoassay, except that in this case they were cut in half and assayed as two 9×15 mm strips. Samples were incubated in 4 ml of 0.5 mgml$^{-1}$ of fibrinogen solution for 10 minutes at room temperature. Sample blanks of uncoated PET strips were incubated in 4 ml of PBS in the same manner. Both samples and blanks were washed in a DiaCent 2000 cell washer and then transferred to clean tubes and incubated with 100 μl PBS and 1 ml m-BCA working reagent at 60° C. A Bovine Serum Albumin (BSA) standard curve was constructed so as to give the required amount of protein in 100 μl solution. Standards were incubated with 1 ml of working reagent as above. The absorbance of a 300 μl aliquot of the sample was measured in a microplate reader at 562 nm.

Abbreviations Used

| Monomer Code | Chemical Name |
|---|---|
| Mpc | Methacryloxyethyl phosphorylcholine (2-methacryloyloxyethyl-2'-trimethylammoniumethyl phosphate inner salt) |
| Bma | Butyl methacrylate (hydrophobic diluent) |
| Tem | 2-trimethylammonium ethyl methacrylate chloride salt |
| Spm | 3-methacryloyloxypropylsulphonate potassium salt |
| EtOH | ethanol |
| TFE | 2,2,2-trifluoroethanol |
| THF | tetrahydrofuran |
| MeOH | methanol |
| DI Water | deionised water |
| DCM | dichloromethane |
| PBS | phosphate buffered saline |
| PET | polyethyleneterephthalate |

EXAMPLE 1

Generic Method for the Preparation of PC-Containing Polyions

The polymers were developed using free radical solution polymerisation techniques following the standard method outlined below. 2-(methacryloyloxyethyl)-2'-(trimethylammoniumethyl) phosphate, inner salt (Mpc) was prepared according to the method described previously WO-A-95/14702. Bma, Spm and Bma are all commercially available.

A triple-necked round bottom flask (500 ml) was equipped with a Davis condenser, a nitrogen inlet and a thermometer. The condenser was topped with a calcium chloride guard tube, and a magnetic follower was added to the flask. The reaction system then purged using nitrogen gas.

The required amount of Mpc was weighed and then stirred in a suitable reaction solvent until dissolved. To this was added the appropriate amounts of the other comonomers (ionic monomer and hydrophobic diluent if required). The initiator type and level was chosen depending upon the reaction solvent employed.

The solutions were then filtered under vacuum using a Buchner funnel, into the reaction vessel. The solution was degassed using a constant flow of nitrogen for a period of twenty minutes, after which time the nitrogen flow rate was reduced and the temperature increased to suitable level dictated by the reaction solvent in use. The polymerisation was carried out under an atmosphere of nitrogen, and maintained at temperature for a period between 16–40 hours.

When the polymerisation had finished the heat source was removed and the solution was allowed to cool to room temperature. In the case where a volatile reaction solvent or solvent mixture had been used, the solvent was removed using rotary evaporation techniques until the point at which the polymer began to foam. This foam was then further redissolved in a suitable solvent/non-solvent combination (typically 9:1 DCM:MeOH) and precipitated by dropwise addition into a non solvent, typically acetone (1000 ml) with constant stirring. The precipitate was then collected using vacuum filtration under a blanket of nitrogen and dried at 50° C. in vacuo for 16 hours.

In the case where water was used as the reaction solvent, the solution was allowed to cool and the polymer purified by ultrafiltration to remove low molecular weight species. The polymer could be isolated by freeze drying for subsequent analysis.

Once isolated, the individual polymers were subjected to NMR and elemental analysis to confirm the structure.

Table 1 summarises the preparative details for a selected range of polyion compounds and Table 2 the isolation details for those polymers. Table 3 provides some characterisation for the polymers in terms of 1H NMR. Elemental analysis was acceptable compared to theoretical values for most cases (within 10% error as expected for polymers); table 4 however, summarises the key elemental data, concentrating on phosphorus:nitrogen and phosphorus:sulphur ratios in order to determine extent of Tem and Spm incorporation in the respective polycations and anions. This can subsequently be used to better define the final polymer composition versus the feed monomer ratios (as shown in table 1 to 3). The inherent viscosity of 20% w/v aqueous solutions of the polyions was obtained by rheometry, as an approximate indicator of molecular weight, and is reported in Table 5.

EXAMPLE 2

Formation of Polyion Complexes (PIC's) by Mixture of Aqueous Solutions of PC-Containing Polyelectrolytes Table 6 summarises some of the observations made upon mixing 20% w/v aqueous solutions of various polyions produced in Example 1 (the ratios are for the monomer in the polymerisation mixture rather than in the polymer by analysis).

0.5 g of each polymer was completely dissolved in 2.5 ml of deionised water to yield a clear solution. One solution of each of the pairs described was poured into the other and then mixed thoroughly with a spatula. In some instances, such as for the poly(Tem)/(Spm) pair, the gelation was almost instantaneous, forming a thick, swollen mass that incorporated all of the water from the system. If this was allowed to stand for a while, the gel could be seen to contract slightly, expelling some of the water from the matrix. It should be noted at this stage, that gels were mixed on an equivalent weight basis rather than using molar proportions (of monomer feed or groups in polymer as analysed).

By talking the observations made in table 6 and plotting them in terms of a ternary phase diagram, it can be seen that there are trends visible (FIG. 1). In polymer systems in which the hydrophobic component is in high, the resulting polymers are water-insoluble and so cannot form a PIC from aqueous solution (although this may still be possible from other solvent systems). In systems where the PC component is high, both the individual polymers and the resulting PIC remain water-soluble. When the correct balance of ionic/hydrophilic/hydrophobic is obtained, a gel is formed as the polyions complex. This gel tends to be 'stiffer' when the hydrophilicity is reduced and when the ionic content is higher.

Figure 2:
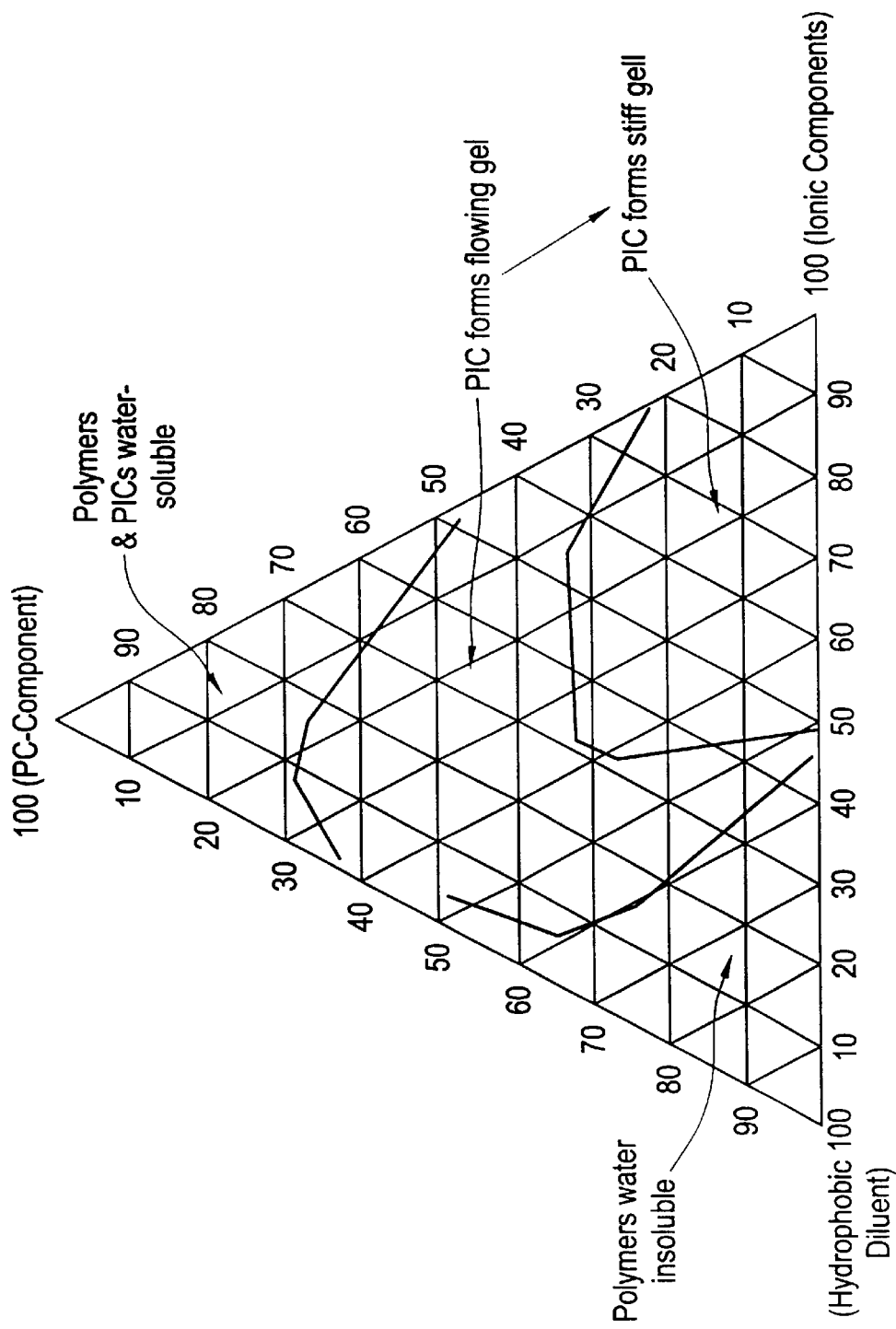
FIG. 2 is a generalised diagram for the formation of polyion complexes.

Thus, a generalisation can be made for the formation of PICs in this type of system (FIG. 2). For the formation of a gel for filling an aneurysm, the properties required from that gel will be such that it remains in place once formed.

EXAMPLE 3

Determination of the Gelation Properties of Polyion Complexes

When considering the ability of a mixture of two polyion solutions to form a gel as described in FIG. 2, it is useful to be able to quantify the observations made. In this instance, 20% (w/v) solutions of the individual polymers were made, mixed together and allowed to settle overnight. The resulting PICs were subjected to a variable torque oscillation test (10–100 mN.m) using a TA Instruments $CSL^2$-100 rheometer fitted with 6 cm 2° cone at 37° C. From this, two parameters could be measured, namely G' the elasticity modulus and G" the viscous modulus. Table 7 summarises the measurements of these parameters for a variety of PIC mixtures, taken at 80 mN.m. The polyions are defined by reference to the monomer ratios used rather than from analysis of ionic groups in the polymer.

Clearly, there a large spread in viscoelastic properties between the different PICs formed. The values are in agreement with the observations expressed in table 6 and reinforce FIGS. 1 & 2. Where values of G' and G" are low, little gelation has occurred when solutions have been mixed. Where these values are higher (ca. >10 Pa), a firm gel of has formed. When the value of G" exceeds that of G', the material has more viscous properties than elastic and it will tend to flow under applied force rather than act elastically. Where G' is greater than G" the opposite is true indicating a more elastic material with a propensity to withstand applied force. This is a useful measure of a material's potential behaviour in a particular application. For an aneurysm-filling material is considered, it would be desirable to obtain a gel that will not wash out of the void under the influence of blood flow.

EXAMPLE 4

Biological Performance of PC-PICs

In order to assess biological performance of the PICs it was necessary to develop a solvent system that would dissolve the complex once formed. PICs are known to be soluble in ternary solvent systems which comprise water, a water-miscible organic solvent and a strongly ionised simple electrolyte. A solubility study was performed on PICs of the described invention and they were found to be soluble in ternary solvent mixtures of water, ethanol and NaCl. A solution of the PIC could then be used to produce reproducible coatings on PET that could be used for biological evaluation. Strips were subjected to a double antibody fibrinogen assay (Fg) and micro bicinchoninic acid protein assay ($\mu$-BCA) in order to gain an appreciation of the extent of protein interaction with the materials. Table 8 summarises the results. Again the polyions are defined by reference to the ratios of monomers used.

From the data it can be seen that coatings of polyion complexes exhibit a lower degree of protein adsorption than the PET control strip. The comparison PlC made from mixing the homopolymers of Tem and Spm (4.3) is less effective at lowering the protein adsorption than those PIC's that contain Mpc. This is consistent with the view that Mpc improves the 'biocompatibility' of surfaces.

TABLE 1

Preparative Details for a Series of Polyions

| Polymer | Solvent | Reaction Time (mins) | Reaction Temp (° C.) | Initiator Type | [Initiator] (%) | Scale (g) | Solids (%) |
| --- | --- | --- | --- | --- | --- | --- | --- |
| MpcTem | D. I. Water | 24 | 80 | APS | 1 | 30 | 15 |
| MpcSpm | D. I. Water | 24 | 80 | APS | 1 | 30 | 15 |
| MpcBmaTem | EtOH | 24 | 70 | AIBN | 1 | 30 | 15 |
| MpcBmaSpm | EtOH | 24 | 70 | AIBN | 1 | 30 | 15 |
| $Mpc_{40}Bma_{40}Tem_{20}$ | THF/EtOH | 18 | 70 | AIBN | 1 | 25 | 12.5 |
| $Mpc_{40}Bma_{40}Spm_{20}$ | TFE | 24 | 70 | AIBN | 1 | 25 | 12.5 |
| $Mpc_{15}Bma_{35}Tem_{50}$ | EtOH | 18 | 70 | AIBN | 1 | 25 | 12.5 |
| $Mpc_{15}Bma_{35}Spm_{50}$ | EtOH | 18 | 70 | AIBN | 1 | 25 | 12.5 |
| $MpcTem_2$ | EtOH | 24 | 60 | AIBN | 0.2 | 15 | 15 |
| BmaSpm | TFE | 40 | 60 | AIBN | 0.4 | 30 | 12.5 |
| $Mpc_{15}Tem_{85}$ | D. I. Water | 24 | 80 | APS | 1 | 25 | 12.5 |
| $Mpc_{15}Spm_{85}$ | D. I. Water | 24 | 80 | APS | 1 | 25 | 12.5 |
| Poly(Tem) | D. I. Water | 24 | 86 | APS | 1 | 25 | 12.5 |
| Poly(Spm) | D. I. Water | 24 | 86 | APS | 1 | 25 | 12.5 |

TABLE 2

Isolation Details for a Series of Polyions

| Polymer | Redissolution Solvents | Precipitation Solvent | Yield (g) | Yield (%) | Appearance | Comments |
|---|---|---|---|---|---|---|
| MpcTem | — | — | 15.8 | 53 | Fine, white powder | Isolated by freeze-drying |
| MpcSpm | — | — | 27 | 90 | Fine, white powder | Isolated by freeze-drying |
| MpcBmaTem | 120 mlDCM/5 mlMeOH | 780 ml Acetone | 22.6 | 75 | Fine, white powder | |
| MpcBmaSpm | 120 mlDCM/5 mlMeOH | 780 ml Acetone | 16.9 | 56 | Grey-white powder | |
| $Mpc_{40}Bma_{40}Tem_{20}$ | — | 200 ml Acetone | 13.8 | 55 | Fine, white powder | |
| $Mpc_{40}Bma_{40}Spm_{20}$ | 140 mlDCM/80 mlTFE | 1.2 l Acetone | 17.3 | 69 | Fine, white powder | |
| $Mpc_{15}Bma_{35}Tem_{50}$ | 120 mlDCM/5 mlMeOH | 780 ml Acetone | 16.3 | 65 | Lumpy white solid | |
| $Mpc_{15}Bma_{35}Spm_{50}$ | 120 mlDCM/5 mlMeOH | 780 ml Acetone | 6.6 | 27 | Lumpy white solid | Difficult to isolate (low Mw?) |
| $MpcTem_2$ | 48 mlDCM/4 mlMeOH | 500 ml Acetone | 13.5 | 95 | White solid | |
| BmaSpm | 50 mlDCM/20 mlTFE | 1.5 l Acetone | 26.8 | 89 | Stringy solid | |
| $Mpc_{15}Tem_{85}$ | — | — | ~22.5 | 90 | White solid | Estimated yield by drying down a sample of solution |
| $Mpc_{15}Spm_{85}$ | — | — | ~22.5 | 90 | White solid | down a sample of solution |
| Poly(Tem) | — | — | ~22.5 | 90 | White solid | Estimated yield by drying |
| Poly(Spm) | — | — | ~22.5 | 90 | White solid | down a sample of solution |

TABLE 3

Summary of $^1$H NMR Data for a Series of Polyions.

| Polyion | Solvent | Description (Peak Position in δ) | Comments |
|---|---|---|---|
| Poly(Spm) | $D_2O$ | 0.9–1.1(3 peaks, b); 1.96(b); 2.15(s); 3.0(triplet, —$CH_2$—S—); 4.15(b) | As expected for structure |
| Poly(Tem) | $D_2O$ | 0.9–1.2(3 peaks, b); 2.05(b); 3.3(s, $N^+(CH_3)_3$); 4.85(m); 4.5(b) | As expected for structure |
| $Mpc_{15}Spm_{85}$ | $D_2O$ | 0.8–1.2(2 peaks, b);1 1.9(b); 2.15(s); 3.0(triplet, —$CH_2$—S—); 3.3(s, $N^+(CH_3)_3$); 3.7; 4.1–4.3(2 peaks, b) | Integration of ($N^+(Me)_3$) vs. —$CH_2$—S gives expected formula |
| $Mpc_{15}Tem_{85}$ | $CD_3OD$ | 0.9–1.3(3 peaks, b); 2.0(b); 3.26 + 3.31(overlapping, $N^+(Me)_3$ from Mpc and Tem); 3.7–4.7(6 peaks, overlapping, b) | Cannot integrate Mpc vs. Tem, peaks to close. |
| MpcBmaSpm | $CD_3OD$ | 0.8–1.3(3 peaks, b); 1.45(—$CH_2$—$CH_3$); 1.65(—O—$CH_2$—$CH_2$—); 1.95; 2.15; 2.9(triplet, —$CH_2$—S—); 3.3(s, $N^+(CH_3)_3$); 3.7; 3.9–4.4(3 peaks, b) | Integration of Mpc vs. Spm and elemental analysis suggests more like ~$Mpc_{25}Bma_{35}Spm_{40}$. Monomer contamination observed. |
| MpcBmaTem | $CD_3OD$ | 0.9–1.2(2 peaks, b); 1.45(—$CH_2$—$CH_3$); 1.65(—O—$CH_2$—$CH_2$—); 1.95 (b); 3.3 + 3.32(overlapping, $N^+(Me)_3$ from Mpc and Tem); 3.7–4.7(8 peaks overlapping, b) | Cannot integrate Mpc vs. Tem, peaks to close. |
| MpcSpm | $D_2O$ | 0.9–1.1(3 peaks, b); 1.9–2.2(5 peaks, b); 2.95(vague triplet, —$CH_2$—S—); 3.3(s, $N^+(CH_3)_3$); 3.7; 4.1–4.4(3 peaks, b) | Integration shows 50:50 Mpc:Spm as expected. |
| MpcTem | $D_2O$ | 0.9–1.3(2 peaks, b); 2.2(b); 3.3 '0 3.33(overlapping, $N^+(Me)_3$ from Mpc and Tem); 3.7, 3.9, 4.1–4.6(3 peaks, b) | Cannot integrate Mpc vs. Tem, peaks to close. |
| BmaSpm | DMSO | 0.7–1.0(2 peaks, b); 1.35(—$CH_2$—$CH_3$); 1.55(—O—$CH_2$—$CH_2$—); 1.85; 2.5(—$CH_2$—S— is masked by DMSO); 3.9(b) | Integration not possible as residual undeuterated DMSO masks Spm. |
| $MpcTem_2$ | $CD_3OD$ | 1.0–1.3(2 peaks, b); 2.15(b); 3.36 + 3.44 33(overlapping, $N^+(Me)_3$ from Mpc and Tem); 3.8–4.7(7 peaks overlapping, b) | Cannot integrate Mpc vs. Tem, peaks to close. |
| $Mpc_{40}Bma_{40}Spm_{40}$ | $CD_3OD$ | 0.8–1.1(3 peaks, b); 1.35(—$CH_2$—$CH_3$); 1.55(—O—$CH_2$—$CH_2$—); 1.8(b); 2.05(b); 2.8 95(triplet, —$CH_2$—'S—); 3.24(s, $N^+(CH_3)_3$); 3.7; 3.9–4.3(4 peaks, b), 4.6 | Integration yields formula as expected. |
| $Mpc_{40}Bma_{40}Tem_{40}$ | $CD_3OD$ | 0.8–1.2(2 peaks, b); 1.35(—$CH_2$—$CH_3$); 1.55(—O—$CH_2$—$CH_2$—); 2.1(b); 3.24 + 3.28(overlapping, $N^+(Me)_3$ from Mpc and Tem)l; 3.6–4.7(7 peaks overlapping, b) | Cannot integrate Mpc vs. Tem, peaks to close. |

TABLE 4

Selected P:N & P:S Ratios for the Confirmation of Polymer Formula (where applicable)
Italics highlight cases where actual results significantly differ form those of the feed ratio.

| Polycation (molar feed ratio) | Mpc | Tem | % Phosphorus | % Nitrogen | Theoretical P:N | Actual P:N | % Mpc | % Tem |
|---|---|---|---|---|---|---|---|---|
| MpcTem | 50 | 50 | 4.8 | 4.9 | 0.904 | 1.021 | 39 | 56.5 |
| MpcBmaTem | 33.3 | 33.3 | 4.28 | 3.9 | 0.904 | 0.911 | 29.7 | 33.6 |
| $Mpc_{40}Bma_{40}Tem_{20}$ | 40 | 20 | 4.28 | 1.84 | 0.678 | 0.43 | *30* | *12.7* |
| $Mpc_{15}Bma_{35}Tem_{20}$ | 15 | 50 | 2.17 | 3.91 | 1.957 | 1.802 | 13.9 | 46 |
| $MpcTem_2$ | 33.3 | 66.7 | 3.2 | 5.05 | 1.356 | 1.578 | *24.4* | *77.5* |
| $Mpc_{15}Tem_{85}$ | 15 | 85 | 1.7 | 5.31 | 3.019 | 3.124 | 12.1 | 87.9 |

TABLE 4-continued

Selected P:N & P:S Ratios for the Confirmation of Polymer Formula (where applicable)
Italics highlight cases where actual results significantly differ form those of the feed ratio.

| Polyanion (molar feed ratio) | Mpc | Spm | % Phosphorus | % Sulphur | Theoretical P:S | Actual P:S | % Mpc | % Spm |
|---|---|---|---|---|---|---|---|---|
| MpcSpm | 50 | 50 | 4.6 | 5.7 | 1.035 | 1.239 | 40.2 | 59.9 |
| MpcBmaSpm | 33.3 | 33.3 | 3.19 | 4.46 | 1.033 | 1.398 | *23.5* | *45.1* |
| $Mpc_{40}Bma_{40}Spm_{20}$ | 40 | 20 | 4.45 | 2.59 | 0.516 | 0.582 | 32.3 | 22.6 |
| $Mpc_{15}Bma_{35}Spm_{20}$ | 15 | 50 | 1.98 | 6.61 | 3.444 | 3.338 | 13.9 | 48.5 |
| $Mpc_{15}Spm_{85}$ | 15 | 85 | 1.75 | 10.5 | 5.869 | 6 | 14.3 | 86.9 |

TABLE 5

Polymer Feed and Final Formulas Based on NMR and Elemental Data Presented in Tables 4 & 5. Where fee ratios differs significantly from final ratio, the formula is shown in italics Inherent Viscosities obtained by Rheometry on 20% w/v Aqueous Solutions of the Polyions.

| Monomer Feed Formula | Suggested Final Polymer Formula | Inherent Viscosity (mPa · s) |
|---|---|---|
| Poly(Tem) | Poly(Tem) | 40 |
| MpcTem | MpcTem | 8.5 |
| MpcBmaTem | MpcBmaTem | 10 |
| $Mpc_{40}Bma_{40}Tem_{20}$ | $Mpc_{30}Bma_{55}Tem_{15}$ | 18 |
| $Mpc_{15}Bma_{35}Tem_{50}$ | $Mpc_{15}Bma_{35}Tem_{50}$ | 14 |
| $MpcTem_2$ | $MpcTem_3$ | 42 |
| $Mpc_{15}Tem_{85}$ | $Mpc_{15}Tem_{85}$ | 71 |
| Poly(Spm) | Poly(Spm) | 300 |
| MpcSpm | MpcSpm | 130 |
| MpcBmaSpm | $Mpc_{25}Bma_{35}Spm_{40}$ | 11 |
| $Mpc_{40}Bma_{40}Spm_{20}$ | $Mpc_{40}Bma_{40}Spm_{20}$ | 6 |
| $Mpc_{15}Bma_{35}Spm_{50}$ | $Mpc_{15}Bma_{35}Spm_{50}$ | 10 |
| BmaSpm | BmaSpm | 14 |
| $Mpc_{15}Spm_{85}$ | $Mpc_{15}Spm_{85}$ | 250 |

TABLE 6

Some Observations Made upon Mixing Aqueous Solutions of Polyions.

| Polycation | Polyanion | Gel Formed? | Appearance | Comments |
|---|---|---|---|---|
| MpcTem | MpcSpm | No | Viscous liquid | |
| $Mpc_{15}Tem_{85}$ | $Mpc_{15}Spm_{85}$ | Yes | Thick gel | Opaque |
| MpcTem | SpmBma | Yes | Flowing gel | Opaque |
| $MpcTem_2$ | SpmBma | Yes | Thick gel | Opaque, expels water |
| MpcBmaTem | MpcBmaSpm | Yes | Flowing gel | Clear |
| $Mpc_{15}Bma_{35}Tem_{50}$ | $Mpc_{15}Bma_{35}Spm_{50}$ | Yes | Gel | Clear |
| $Mpc_{40}Bma_{40}Tem_{20}$ | $Mpc_{40}Bma_{40}Spm_{20}$ | Yes | Flowing gel | Opaque |
| MpcBmaTem | MpcSpm | No | Viscous liquid | |
| MpcTem | MpcBmaSpm | No | Viscous liquid | |
| $Mpc_{20}Bma_{60}Tem_{20}$ | $Mpc_{20}Bma_{60}Spm_{20}$ | — | — | Polymers water-insoluble |
| Poly(Tem) | Poly(Spm) | Yes | Very thick gel | Opaque, expels water |

TABLE 7

Viscoelastic Properties of Selected PIC gels

| Polycation | Polyanion | G' (Pa) | G" (Pa) |
|---|---|---|---|
| MpcTem | BmaSpm | 3.25 | 30 |
| MpcTem | BmaSpm | 600 | 800 |
| MpcTem | MpcSpm | 0.15 | 3.5 |
| MpcTem | MpcBmaSpm | 0.025 | 0.48 |
| MpcBmaTem | MpcSpm | 0.3 | 4 |
| MpcBmaTem | MpcBmaSpm | 50 | 45 |
| $Mpc_{15}Bma_{35}Tem_{50}$ | $Mpc_{15}Bma_{35}Spm_{50}$ | 400 | 150 |
| $Mpc_{15}Tem_{85}$ | $Mpc_{15}Spm_{85}$ | 1500 | 1000 |
| $Mpc_{40}Bma_{40}Tem_{20}$ | $Mpc_{40}Bma_{40}Spm_{20}$ | 85 | 125 |
| Poly(Tem) | Poly(Spm) | 9000 | 4500 |

TABLE 8

Estimation of Adsorbed Protein for PIC Coatings Using Fibrinogen (Fg) and bicinchoniic acid ($\mu$-BCA) Assays (Uncoated PET strip control)

| No | Polyion Complex Pair | Bioevaluation Test Method | % Reduction of Adsorbed Protein |
|---|---|---|---|
| 4.1 | MpcBmaTem + MpcBmaSpm | Fg (n = 7) | 77.8 |
| 4.2 | $Mpc_{15}Bma_{35}Tem_{50}$ + $Mpc_{15}Bma_{35}Spm_{50}$ | Fg (n = 7) | 77.7 |
| 4.3 | Poly(Tem) + Poly(Spm) | Fg (n = 7) | 47.1 |
| 4.1 | MpcBmaTem + MpcBmaSpm | $\mu$-BCA (n = 5) | 82.4 |
| 4.2 | $Mpc_{15}Bma_{35}Tem_{50}$ + $Mpc_{15}Bma_{35}Spm_{50}$ | $\mu$-BCA (n = 4) | 61.8 |
| 4.3 | Poly(Tem) + Poly(Spm) | $\mu$-BCA (n = 3) | 33.7 |

What is claimed is:

1. Method of treatment of an animal by therapy or diagnosis including the steps:
   a. providing a charged polymer containing composition which comprises a solvent and a charged polymer having a zwitterionic pendant groups in solution in the solvent;
   b. providing a counterion composition comprising a solvent and a polyvalently charged ion of opposite charge to that of the said charged polymer in solution in the solvent;
   c. introducing the charged polymer containing composition and the counterion composition into a body cavity of the animal; and
   d. contacting the charged polymer containing composition with the counterion composition whereby the charged polymer is rendered insoluble, forming a gel comprising a matrix of insoluble polymer and solvent distributed throughout the matrix in the body cavity.

2. Method according to claim 1 in which agent which is a therapeutically active agent or a diagnostic agent is incorporated into the insoluble polymer.

3. Method according to claim 2 which the agent is a diagnostic imaging agent.

4. Method according to claim 1 in which the body cavity is a blood vessel.

5. Method according to claim 4 in which the insoluble polymer embolises a vein or packs an aneurysm.

6. Method according to claim 1 in which the charged polymer in the charged polymer composition is water soluble.

7. Method according to claim 6 in which the solvent in the charged polymer composition consists of water.

8. Method according to claim 1 in which the counterion is a polyelectrolyte.

9. Method according to claim 8 in which the polyelectrolyte has pendant zwitterionic groups.

10. Method according to claim 1 in which the or each zwitterionic pendant group has the general formula IV

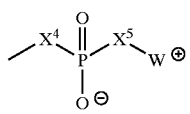

IV in which the moieties $X^4$ and $X^5$, which are the same or different, are selected from the group consisting of —O—, —S—, —NH— and a valence bond and $W^+$ is a group comprising an ammonium, phosphonium or sulphonium cationic group and a group linking the anionic and cationic moieties which is a $C_{1-12}$-alkanediyl group.

11. Method according to claim 10 in which W is selected from the group consisting of $W^1$—$N^+R^8_3$, —$W^1$—$P^+R^9_3$, —$W^1$—$S^+R^9_2$ and —$W^1$-Het$^+$ in which:

$W^1$ is selected from the group consisting of alkanediyl of 1 or more carbon atoms optionally containing one or more ethylenically unsaturated double or triple bonds, disubstituted-aryl, alkylene aryl, aryl alkylene, alkylene aryl alkylene, disubstituted cycloalkyl, alkylene cycloalkyl, cycloalkyl alkylene and alkylene cycloalkyl alkylene, optionally containing one or more fluorine substituents and/or one or more functional groups; and either the groups $R^8$ are the same or different and each is selected from the group consisting of hydrogen, alkyl of 1 to 4 carbon atoms and aryl, or two of the groups $R^8$ together with the nitrogen atom to which they are attached form a heterocyclic ring containing from 5 to 7 atoms or the three groups $R^8$ together with the nitrogen atom to which they are attached form a fused ring structure containing from 5 to 7 atoms in each ring, and optionally one or more of the groups $R^8$ is substituted by a hydrophilic functional group, and the groups $R^9$ are the same or different and each is $R^8$ or a group $OR^8$, where $R^8$ is as defined above; and Het is an aromatic nitrogen-, phosphorus- or sulphur-containing ring.

12. Method according to claim 11 in which $W^1$ is a straight-chain alkanediyl group.

13. Method according to claim 10 in which the or each zwitterion is a group of formula V:

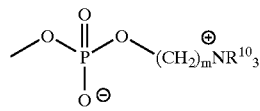

V where the groups $R^{10}$ are the same or different and each is hydrogen or $C_{1-4}$ alkyl, and m is from 1 to 4.

14. Method according to claim 1 in which the zwitterionic pendant groups are derived from a monomer of the formula VI Y—B—X  VI wherein B is selected from the group consisting of straight and branched alkanediyl, alkanediyloxaalkanediyl and alkanediyloligo(oxaalkanediyl) chain optionally containing one or more fluorine atoms and if X or Y contains a terminal carbon atom bonded to B, a valence bond;

X is the zwitterionic group; and

Y is an ethylenically unsaturated polymerisable group selected from the group consisting of

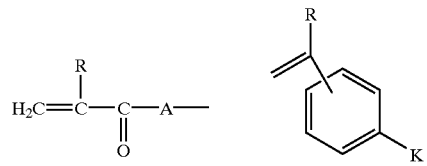

$CH_2$=$C(R)$—$CH_2$—O—, $CH_2$=$C(R)$—$CH_2OC(O)$—, $CH_2$=$C(R)OC(O)$—, $CH_2$=$C(R)$—O—, $CH_2$=$C(R)CH_2OC(O)N(R^{11})$—, $R^{12}OOCCR$=$CRC(O)$—O—, $RCH$=$CHC(O)O$—, $RCH$=$C(COOR^{12})CH_2$—$C(O)$—O—,

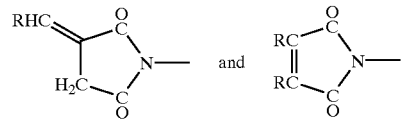 and wherein:

R is hydrogen or a $C_1$–$C_4$ alkyl group;

$R^{11}$ is hydrogen or a $C_1$–$C_4$ alkyl group or $R^{11}$ is —B—X where B and X are as defined above;

$R^{12}$ is hydrogen or a $C_{1-4}$ alkyl group or BX where B and X are as defined above;

A is —O— or —$NR^{11}$—; and

K is selected from the group consisting of —$(CH_2)_pOC(O)$—, —$(CH_2)_pC(O)O$—, —$(CH_2)_pOC(O)O$—, —$(CH_2)_pNR^{13}$—, —$(CH_2)_pNR^{13}C(O)$—, —$(CH_2)_pC(O)NR^{13}$—, —$(CH_2)_pNR^{13}C(O)O$—, —$(CH_2)_pOC(O)NR^{13}$—, —$(CH_2)_pNR^{13}C(O)NR^{13}$— (in which the groups $R^{13}$ are the same or different), —$(CH_2)_pO$—, —$(CH_2)_pSO_3$—, and optionally in combination with B, a valence bond and p is from 1 to 12 and $R^{13}$ is hydrogen or a $C_1$–$C_4$ alkyl group.

15. Method according to claim 14 in which Y is $CH_2$=$C(R)COA$ in which R is hydrogen or methyl and A is O.

16. Method according to claim 14 in which B is $C_{1-12}$-alkylene.

17. Method according to claim 1 in which the charged polymer is formed from ethylenically unsaturated monomers including a monomer of the general formula VII $$Y^1B^1Q \qquad \qquad VII$$

in which

Y$^1$ is an ethylenically unsaturated polymerisable group selected from the group consisting of

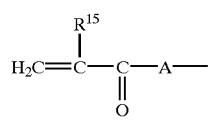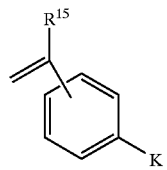

CH$_2$=C(R$^{15}$)—CH$_2$—O—, CH$_2$=C(R$^{15}$)—CH$_2$OC(O)—, CH$_2$=C(R$^{15}$)OC(O)—, CH$_2$=C(R$^{15}$)—O—, CH$_2$=C(R$^{15}$)CH$_2$OC(O)N(R$^{16}$)—, R$^{17}$OOCCR$^{15}$=CR$^{15}$C(O)—O—, R$^{15}$CH=CHC(O)O—, R$^{15}$CH=C(COOR$^{17}$)CH$_2$—C(O)—O—,

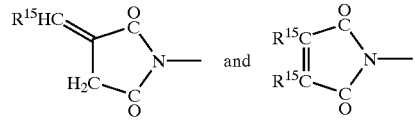 and 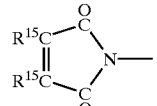

wherein:

R$^{15}$ is hydrogen or a C$_1$–C$_4$ alkyl group;

R$^{16}$ is hydrogen or a C$_1$–C$_4$ alkyl group or R$^{16}$ is —B$^1$—Q where B$^1$ and Q are as defined below;

R$^{17}$ is hydrogen or a C$_{1-4}$ alkyl group;

A is —O— or —NR$^{16}$—;

K is selected from the group consisting of —(CH$_2$)$_r$OC(O)—, —(CH$_2$)$_r$C(O)O—, —(CH$_2$)$_r$OC(O)O—, (CH$_2$)$_r$NR$^{18}$—, —(CH$_2$)$_r$NR$^{18}$C(O)—, —(CH$_2$)$_r$C(O)NR$^{18}$—, —(CH$_2$)$_r$NR$^{18}$C(O)O—, —(CH$_2$)$_r$OC(O)NR$^{18}$—, —(CH$_2$)$_r$NR$^{18}$C(O)NR$^{18}$— (in which the groups R$^{18}$ are the same or different), —(CH$_2$)$_r$O—, —(CH$_2$)$_r$SO$_3$—, and optionally in combination with B$^1$, a valence bond and r is from 1 to 12 and R$^{18}$ is hydrogen or a C$_1$–C$_4$ alkyl group;

B$^1$ is selected from the group consisting of straight or branched alkanediyl, alkanediyloxaalkanediyl or alkanediyloligo(oxaalkanediyl) and optionally containing one or more fluorine atoms and if Q or Y$^1$ contains a terminal carbon atom bonded to B$^1$, a valence bond; and Q is a cationic or an anionic group.

18. Method according to claim 17 in which Q is a cationic group Q$^1$ which is selected from the group consisting of N$^+$R$^1_3$, P$^+$R$^1_3$ and S$^+$R$^1_2$ in which the groups R$^1$ are the same or different and are each selected from the group consisting of hydrogen, C$_{1-4}$-alkyl and aryl or two of the groups R$^1$ together with the heteroatom to which they are attached from a saturated or unsaturated heterocyclic ring containing from 5 to 7 atoms.

19. Method according to claim 8 in which the polyelectrolyte is formed from ethylenically unsaturated monomers including a monomer of the general formula VII $$Y^1B^1Q \qquad \qquad VII$$

in which

Y$^1$ is an ethylenically unsaturated polymerisable group selected from the group consisting of

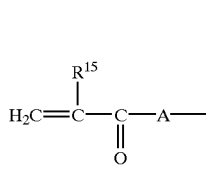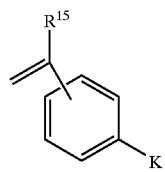

CH$_2$=C(R$^{15}$)—CH$_2$—O—, CH$_2$=C(R$^{15}$)—CH$_2$OC(O)—, CH$_2$=C(R$^{15}$)OC(O)—, CH$_2$=C(R$^{15}$)—O—, CH$_2$=C(R$^{15}$)CH$_2$OC(O)N(R$^{16}$)—, R$^{17}$OOCCR$^{15}$=CR$^{15}$C(O)—O—, R$^{15}$CH=CHC(O)O—, R$^{15}$CH=C(COOR$^{17}$)CH$_2$—C(O)—O—,

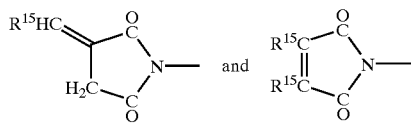 and 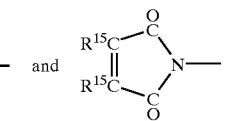

wherein:

R$^{15}$ is hydrogen or a C$_1$–C$_4$ alkyl group;

R$^{16}$ is hydrogen or a C$_1$–C$_4$ alkyl group or R$^{16}$ is —B$^1$—Q where B$^1$ and Q are as defined below;

R$^{17}$ is hydrogen or a C$_{1-4}$ alkyl group;

A is —O— or —NR$^{16}$—;

K is selected from the group consisting of —(CH$_2$)$_r$OC(O)—, —(CH$_2$)$_r$C(O)O—, —(CH$_2$)$_r$OC(O)O—, (CH$_2$)$_r$NR$^{18}$—, —(CH$_2$)$_r$NR$^{18}$C(O)—, —(CH$_2$)$_r$C(O)NR$^{18}$—, —(CH$_2$)$_r$NR$^{18}$C(O)O—, —(CH$_2$)$_r$OC(O)NR$^{18}$—, —(CH$_2$)$_r$NR$^{18}$C(O)NR$^{18}$— (in which the groups R$^{18}$ are the same or different), —(CH$_2$)$_r$O—, —(CH$_2$)$_r$SO$_3$—, and optionally in combination with B$^1$, a valence bond and r is from 1 to 12 and R$^{18}$ is hydrogen or a C$_1$–C$_4$ alkyl group;

B$^1$ is selected from the group consisting of straight or branched alkanediyl, alkanediyloxaalkanediyl or alkanediyloligo(oxaalkanediyl) and optionally containing one or more fluorine atoms and if Q or Y$^1$ contains a terminal carbon atom bonded to B$^1$, a valence bond; and Q is a cationic or an anionic group.

20. Method according to claim 19 in which the ethylenically unsaturated monomer also includes a monomer of the general formula VI $$Y—B—X \qquad \qquad VI$$

wherein

B is selected from the group consisting of straight and branched alkanediyl, alkanediyloxaalkanediyl and alkanediyloligo(oxaalkanediyl) chain optionally containing one or more fluorine atoms and if X or Y contains a terminal carbon atom bonded to B, a valence bond;

X is the zwitterionic group; and

Y is an ethylenically unsaturated polymerisable group selected from the group consisting of

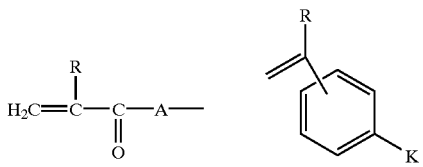

CH$_2$=C(R)—CH$_2$—O—, CH$_2$=C(R)—CH$_2$OC(O)—, CH$_2$=(R)OC(O)—, CH$_2$=C(R)—O—, CH$_2$=C(R)CH$_2$OC(O)N(R$^{11}$)—, R$^{12}$OOCCR=CRC(O)—O—, RCH=CHC(O)O—, RCH=C(COOR$^{12}$)CH$_2$—C(O)—O—,

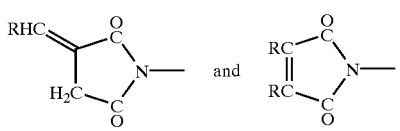

wherein:

R is hydrogen or a C$_1$–C$_4$ alkyl group;

R$^{11}$ is hydrogen or a C$_1$–C$_4$ alkyl group or R$^{11}$ is —B—X where B and X are as defined above;

R$^{12}$ is hydrogen or a C$_{1-4}$ alkyl group or BX where B and X are as defined above;

A is —O— or —NR$^{11}$—; and

K is selected from the group consisting of —(CH$_2$)$_p$OC(O)—, —(CH$_2$)$_p$C(O)O—, —(CH$_2$)$_p$OC(O)O—, —(CH$_2$)$_p$NR$^{13}$—, —(CH$_2$)$_p$NR$^{13}$C(O)—, —(CH$_2$)$_p$C(O)NR$^{13}$—, —(CH$_2$)$_p$NR$^{13}$C(O)O—, —(CH$_2$)$_p$OC(O)NR$^{13}$—, —(CH$_2$)$_p$NR$^{13}$C(O)NR$^{13}$— (in which the groups R$^{13}$ are the same or different), —(CH$_2$)$_p$O—, —(CH$_2$)$_p$SO$_3$—, and optionally in combination with B, a valence bond and p is from 1 to 12 and R$^{13}$ is hydrogen or a C$_1$–C$_4$ alkyl group.

21. Method according to claim 19 in which Q is an anionic group Q$^2$ selected from the group consisting of carboxylate, carbonate, sulphate, sulphonate, phosphate and phosphonate.

22. Method according to claim 14 in which the ethylenically unsaturated monomers from which the charged polymer or the counterionic polyelectrolyte are formed comprise nonionic monomer of the general formula VIII

Y$^2$R$^{14}$      VIII in which

Y$^2$ is an ethylenically unsaturated polymerisable group selected from the group consisting of

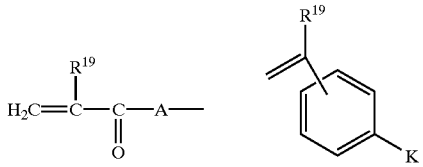

CH$_2$=C(R$^{19}$)—CH$_2$—O—, CH$_2$=C(R$^{19}$)—CH$_2$OC(O)—, CH$_2$=C(R$^{19}$)OC(O)—, CH$_2$=C(R$^{19}$)—O—, CH$_2$=C(R$^{19}$)CH$_2$OC(O)N(R$^{20}$)—, R$^{21}$OOCCR$^{19}$=CR$^{19}$C(O)—O—, R$^{19}$CH=CHC(O)O—, R$^{19}$CH=C(COOR$^{21}$)CH$_2$—C(O)—O—,

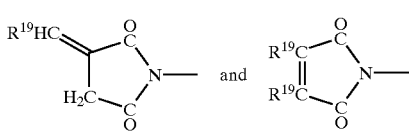

wherein:

R$^{19}$ is hydrogen or a C$_1$–C$_4$ alkyl group;

R$^{20}$ is hydrogen or a C$_1$–C$_4$ alkyl group or R$^{20}$ is R$^{14}$;

R$^{21}$ is hydrogen or a C$_{1-4}$ alkyl group or R$^{14}$;

A is —O— or —NR$^{20}$—;

K is selected from the group consisting of —(CH$_2$)$_s$OC(O)—, —(CH$_2$)$_s$C(O)O—, —(CH$_2$)$_s$OC(O)O—, —(CH$_2$)$_s$NR$^{22}$—, —(CH$_2$)$_s$NR$^{22}$C(O)—, —(CH$_2$)$_s$C(O)NR$^{22}$—, —(CH$_2$)$_s$NR$^{22}$C(O)O—, —(CH$_2$)$_s$OC(O)NR$^{22}$—, —(CH$_2$)$_s$NR$^{22}$C(O)NR$^{22}$— (in which the groups R$^{22}$ are the same or different), —(CH$_2$)$_s$O—, —(CH$_2$)$_s$SO$_3$—, and a valence bond and s is from 1 to 12 and R$^{22}$ is hydrogen or a C$_1$–C$_4$ alkyl group; and R$^{14}$ is selected from the group consisting of C$_{1-24}$-alkyl and -alkenyl groups optionally substituted by a substituent selected from the group consisting of hydroxyl groups; halogen atoms; alkoxy and oligo-alkoxy groups, in which the alkoxy groups have 1–6, carbon atoms; aryl groups, acyl; acyloxy; and acylamino groups.

23. Method according to claim 22 in which Y$^2$ is CH$_2$=C(CH$_3$)CO and R$^{14}$ is an unsubstituted C$_{1-18}$-alkyl or -alkenyl group.

24. Method according to claim 22 in which diluent monomer is included in the ethylenically unsaturated monomer in molar amount in the range 1 to 75%.

25. Method according to claim 17 in which the mole ratio of zwitterionic monomer to ionic monomer of the formula VII is in the range 5:1 to 1:5, and in which the total molar amount of zwitterionic monomer and ionic monomer in the ethylenically unsaturated monomers is in the range 25 to 100%.

26. Method according to claim 1 in which the ratio of equivalents of charged groups in the charged polymer to counterionic groups in the counterion is in the range 2:1 to 1:2.

27. Method of treatment of an animal by therapy or diagnosis including the steps:

providing a water soluble, charged polymer containing composition which comprises a solvent and a charged polymer having zwitterionic pendant groups in solution in the solvent;

providing a counterion composition comprising a solvent and a polyelectrolyte of opposite charge to that of the charged polymer in solution in the solvent, the ratio of equivalents of charged groups in the charged polymer to counterionic groups in the polyelectrolytes being in the range of 2:1 to 1:3;

introducing the charged polymer containing composition and the counterion composition into a body cavity of the animal; and contacting the charged polymer containing composition with the counterion composition whereby the charged polymer is rendered insoluble, forming a gel comprising a matrix of insoluble polymer and solvent distributed throughout the matrix in the body cavity.

28. Method according to claim 8, wherein the counterion composition is aqueous.

* * * * *